(12) United States Patent
Hopkins

(10) Patent No.: US 12,721,935 B2
(45) **Date of Patent: *Sep. 1, 2026**

(54) ROBUST NITRIC OXIDE-RELEASING POLYMERS AND ARTICLES AND METHODS OF MAKING AND USES THEREOF

(71) Applicant: University of Georgia Research Foundation, Inc., Athens, GA (US)

(72) Inventor: Sean Hopkins, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 815 days.

This patent is subject to a terminal disclaimer.

(21) Appl. No.: 17/259,817

(22) PCT Filed: Jul. 16, 2019

(86) PCT No.: PCT/US2019/041925

§ 371 (c)(1),
(2) Date: Jan. 12, 2021

(87) PCT Pub. No.: WO2020/018488

PCT Pub. Date: Jan. 23, 2020

(65) Prior Publication Data

US 2021/0268156 A1 Sep. 2, 2021

Related U.S. Application Data

(60) Provisional application No. 62/698,840, filed on Jul. 16, 2018.

(51) Int. Cl.
*A61K 33/00* (2006.01)
*A61L 27/34* (2006.01)
(Continued)

(52) U.S. Cl.
CPC ......... *A61L 33/0041* (2013.01); *A61L 33/062* (2013.01); *A61L 27/48* (2013.01);
(Continued)

(58) Field of Classification Search
None
See application file for complete search history.

(56) References Cited

U.S. PATENT DOCUMENTS 3,959,327 A 5/1976 Pepe et al.
7,491,846 B2 2/2009 Aoki et al.
(Continued)

FOREIGN PATENT DOCUMENTS

WO 2011022680 A2 2/2011
WO WO2014124125 A2 8/2014
(Continued)

OTHER PUBLICATIONS

International Search Report and Written Opinion for International Application No. PCT/US19/41925, mailed Sep. 10, 2019.
(Continued)

*Primary Examiner* — Kyung S Chang
(74) *Attorney, Agent, or Firm* — Thomas | Horstemeyer, LLP

(57) ABSTRACT

Described herein are nitric oxide releasing materials, methods of making nitric oxide releasing materials, and devices including nitric oxide releasing materials. The nitric oxide releasing material includes a polymer matrix having a plurality of polysiloxanes and nitric oxide-donating crosslinking moieties that covalently crosslink the polysiloxanes. Blood clotting or adhesion of a biomaterial to a surface, as well as biofilm formation can be prevented using the methods and materials described.

26 Claims, 6 Drawing Sheets

(51) Int. Cl.

| | |
|---|---|
| ***A61L 27/48*** | (2006.01) |
| ***A61L 27/54*** | (2006.01) |
| ***A61L 29/08*** | (2006.01) |
| ***A61L 29/12*** | (2006.01) |
| ***A61L 29/16*** | (2006.01) |
| ***A61L 31/10*** | (2006.01) |
| ***A61L 31/12*** | (2006.01) |
| ***A61L 31/16*** | (2006.01) |
| ***A61L 33/00*** | (2006.01) |
| ***A61L 33/06*** | (2006.01) |
| ***C01B 21/24*** | (2006.01) |

(52) U.S. Cl.

CPC ............. *A61L 27/54* (2013.01); *A61L 29/126* (2013.01); *A61L 29/16* (2013.01); *A61L 31/129* (2013.01); *A61L 31/16* (2013.01); *A61L 2300/114* (2013.01); *A61L 2430/20* (2013.01)

(56) References Cited

U.S. PATENT DOCUMENTS

| | | | |
|---|---|---|---|
| 7,524,989 | B2 | 4/2009 | Williams |
| 8,545,789 | B2 | 10/2013 | Yang et al. |
| 9,120,814 | B2 | 9/2015 | Park et al. |
| 9,440,953 | B2 | 9/2016 | Golebiowski et al. |
| 9,499,511 | B2 | 11/2016 | Toscano et al. |
| 9,884,943 | B2 | 2/2018 | Frost et al. |
| 10,179,330 | B2 | 1/2019 | Srivastava et al. |
| 10,442,812 | B2 | 10/2019 | Krainc et al. |
| 10,457,662 | B2 | 10/2019 | Neamati et al. |
| 10,472,345 | B2 | 11/2019 | Dumas et al. |
| 2011/0059036 | A1 | 3/2011 | Arnold et al. |
| 2011/0244001 | A1* | 10/2011 | Mather .................... C08J 5/046 977/788 |
| 2012/0134951 | A1 | 5/2012 | Stasko et al. |
| 2014/0012080 | A1 | 1/2014 | Wada et al. |
| 2015/0238662 | A1 | 8/2015 | Handa et al. |
| 2015/0247005 | A1 | 9/2015 | Frost et al. |
| 2017/0018082 | A1 | 1/2017 | Hu et al. |
| 2017/0028106 | A1 | 2/2017 | Brisbois et al. |
| 2018/0214598 | A1 | 8/2018 | Stasko et al. |
| 2021/0268156 | A1 | 9/2021 | Handa et al. |
| 2024/0131231 | A1 | 4/2024 | Handa et al. |
| 2024/0139385 | A1 | 5/2024 | Handa et al. |
| 2025/0129265 | A1 | 4/2025 | Brisbois et al. |

FOREIGN PATENT DOCUMENTS

| | | | |
|---|---|---|---|
| WO | 20170180822 | A1 | 10/2017 |
| WO | 2020/018488 | A1 | 1/2020 |
| WO | WO2022018488 | A1 | 1/2022 |
| WO | WO2022169741 | A1 | 8/2022 |

OTHER PUBLICATIONS

International Search Report and Written Opinion for International Application No. PCT/US2019/047749, mailed Dec. 27, 2019.

Starett, Michael A., "Development of a wireless platform to generate nitric oxide for implanted biomedical devices", Master's Thesis, Michigan Technological University, 2010. https://digitalcommons.mtu.edu/etd-restricted/30.

Gierke, et al., S-Nitroso-N-acetyl-D-penicilliamine covalentry Linked to polydimethylsiloxane (SNAP-PDMS) for use as a controlled photoinitiated nitric oxide release polymer., 2011 Sci. Technol. Adv. Mater. 12 055007.

Office Action for European Application 19852304.5-1109 mailed Aug. 22, 2025.

Yaqi Wo et al.: "Recent advances in thromboresistant and antimicrobial polymers for biomedical applications: just say yes to nitric oxide (NO)", Biomaterials Science, vol. 4, No. 8, Jan. 1, 2016 (Jan. 1, 2016), pp. 1161-1183, XP055688036.

Extended European Search Report for application PCT/U.S. Pat. No. 2022076627 mailed Jul. 9, 2025.

International Search Report dated Jan. 24, 2023 for application No. PCT/US2022/076627.

Adam et al. Reaction of 1,2-Dioxetanes with Heteroatom Nucleophiles: Adduct Formation by Nucleophilic Attack at the Peroxide Bond. J _Am. Chem. Soc. 1992, 114, 5591-5598.

Adam et al. Reaction of r-Peroxy Lactones with C, N, P, and S Nucleophiles: Adduct Formation and Nucleophile :: Oxidalion by Nucleophilic Attack at and Biphilic Insertion into the Peroxide Bond. J.Org. Chem. 1997, 62, 1623-1629.

Extended European Search Report Application No. 19838396.8 mailed Mar. 16, 2022.

Miura, Y .; et al. Syntheses of Stable N-tert-Alkoxyarylaminyl Mono- and Diradicals by the Reaction of the Lithium Salts of 2,4,6-Trisubslituted Anilines with tert-Alkyl Mono- and Diperoxybenzoates. J_ Org. Chem. 2005, 70, 4177-4179.

Miura, Y.; et al. Isolation and Magnetic Properties of Heterocycle-Carrying N-Alkoxyarylaminyl Radicals. J_ Org. Chem. 2003, 68, 10158-10161.

Miura, Y.; et al. First Isolation of N-Alkoxyaminyl Radicals. Chem. Commun. 2001, 627-628.

Meesters, AC. M.; et al. The Direct Synthesis of N-t-Alkyl-O-1-butylhydroxylamines from I-Butyl Peroxybenzoate and the Lithium Salts of Primary 1-Alkylamines. Synthesis 1978, 9, 679-680.

Kelly, D. R. et al. The Mechanism of the Tertiary Amine Catalysed Isomerization of Endoperoxides to Hydroxyketones: Synthesis and Chemistry of the Intermediate Postulated in the Peroxide Attack Mechanism. Tetrahedron Lett. 2002, 13, 9331.

Biloski, A J_ et al. Improved Oxidation of Amines with Dibenzoyl Peroxide. Synthesis 1983, 7, 537.

Banerjee, A et al. Direct N—O Bond Formation via Oxidation of Amines with Benzoyl Peroxide. Chem. Sci. 2019, 10, 2124.

(Pawar, Bet al.) n-Dodecylbenzene Sulfonic Acid (DBSA) as a Novel Bronsted Acid Catalyst for the Synthesis of Bis (indolyl)methanes and Bis(4-hydroxycoumarin-3-yl)methanes in Water. Green and Sustainable Chemistry, vol. 3, 2013, DOI: 10.4236/gsc.2013.32010, pp. 56-60; abstract.

International Search Report and Written Opinion for International Application No. PCT/US22/14689 mailed Apr. 14, 2022.

Sean P. Hopkins, Jitendra Pant, Marcus J. Goudie, Chad Schmiedt, and Hitesh Handa ACS Applied Materials & Interfaces 2018 10 (32), 27316-27325.

* cited by examiner

NO Surface Flux (x10$^{-10}$ mol cm$^{-2}$ min$^{-1}$)
Time (Days)
0 1 3 5 7 10 14 17 21 25 28 31 35 38 43 51 58 63 82 86 90 97 104 111 118 125
NO Surface Flux
Time (Days)
82 86 90 97 104 111 118 125

Total NO Release (μmol cm$^{-2}$)
Time (Days)

NO Surface Flux (x10$^{-10}$ mol cm$^{-2}$ min$^{-1}$)
Time (Minutes)

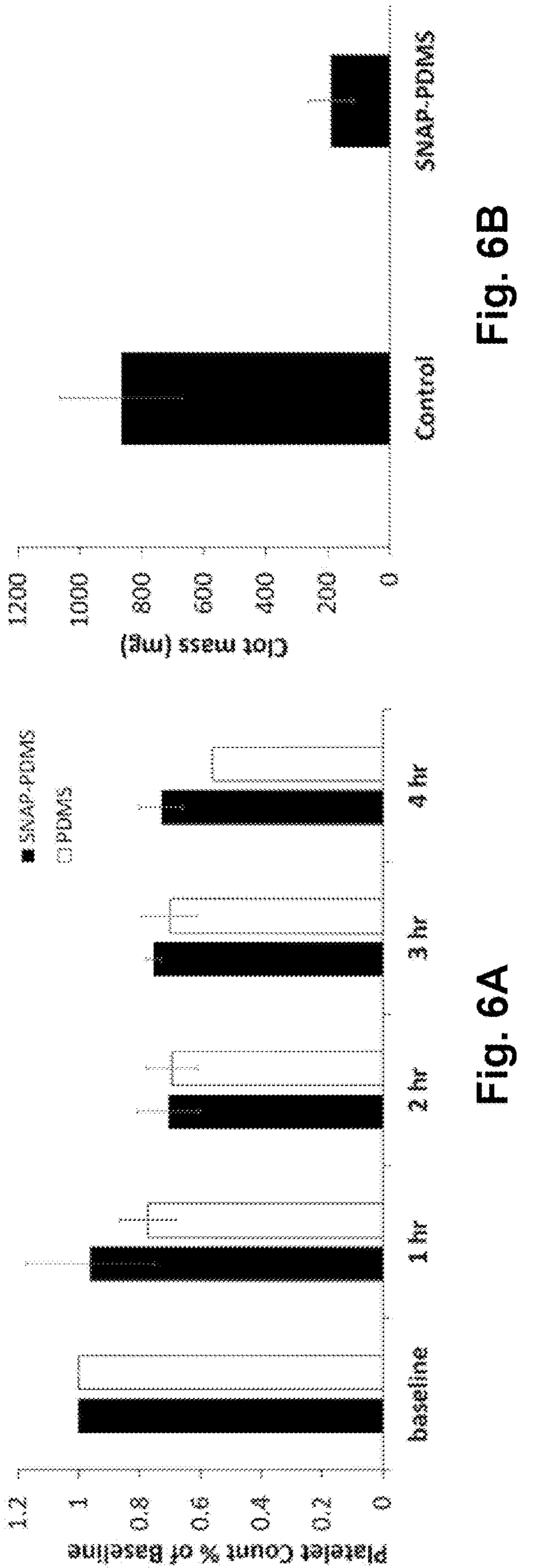
Fig. 6A
Fig. 6B
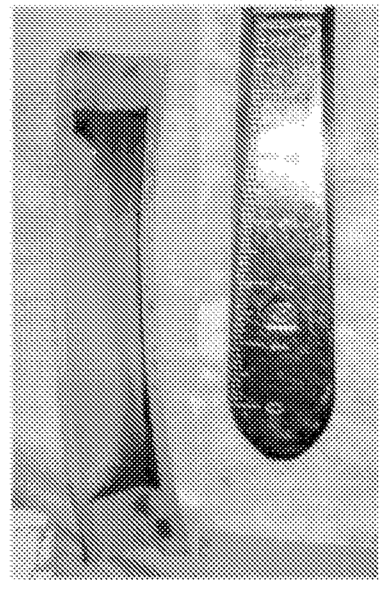
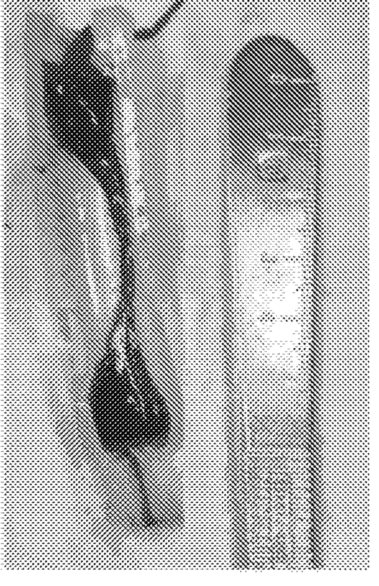
Fig. 6C

ROBUST NITRIC OXIDE-RELEASING POLYMERS AND ARTICLES AND METHODS OF MAKING AND USES THEREOF

CROSS-REFERENCE TO RELATED APPLICATIONS

This application claims the benefit of and priority to U.S. Provisional Application Ser. No. 62/698,840, having the title "ROBUST NITRIC OXIDE-RELEASING POLYMERS AND ARTICLES AND METHODS OF MAKING AND USES THEREOF", filed on Jul. 16, 2018, the disclosure of which is incorporated herein by reference in its entirety.

STATEMENT REGARDING FEDERALLY SPONSORED RESEARCH OR DEVELOPMENT

This invention was made with government support under awards K25HL111213 and R01HL134899 awarded by the National Institutes of Health and award 200-2016-91933 awarded by Centers for Disease Control and Prevention. The government has certain rights in the invention.

TECHNICAL FIELD

The present disclosure generally relates to nitric oxide-releasing polymeric materials.

BACKGROUND

When a foreign material or medical device comes in contact with blood, proteins such as albumin and fibrinogen immediately adsorb to the surface to facilitate the attachment of platelets. Once attached, platelets directly interact with the adsorbed proteins, exposing the glycoprotein GPIIb/IIIa integrin receptor that allows platelet binding to fibrinogen.[1] This facilitates more platelet activation and aggregation to form a clot. In addition to reducing the efficiency of the implant, these clots also have a risk of breaking off and causing embolism further down the vasculature. Infection is another complication that occurs with medical devices in a clinical setting. The longer devices such as catheters and endotracheal tubes stay within a patient, the higher the risk of an infection.[2] This leads to constant removal and replacement of these devices, requiring invasive surgeries and overall discomfort to the patient.

There remains a need for improved materials, articles, and methods that overcome the aforementioned deficiencies.

SUMMARY

Embodiments of the present disclosure provide for nitric oxide releasing materials, methods of making nitric oxide releasing materials, and devices including nitric oxide releasing materials.

An aspect of the present disclosure includes a nitric oxide releasing material including a polymer matrix. The polymer matrix can include a plurality of polysiloxanes. The polymer matrix can also include a plurality of nitric oxide-donating crosslinking moieties that covalently crosslink polysiloxanes in the plurality of polysiloxanes. The nitric oxide-donating crosslinking moieties can be present in an equimolar amount of covalently attached SNAP is present with respect to the crosslinking agent. The nitric oxide-donating crosslinking moieties can be present in an amount from about 0.1 micromoles to about 0.801 micromoles, from about 0.1 micromoles, about 0.2 micromoles, about 0.3 micromoles, or about 0.35 micromoles or greater per milligram of the polymer matrix. Each of the oxide-donating crosslinking moieties in the plurality of nitric oxide-donating crosslinking moieties can have S-nitroso-N-acetyl-penicillamine groups covalently attached thereto.

Another aspect of the present disclosure includes a nitric oxide releasing material including a polymer matrix. The polymer matrix can include a plurality of polysiloxanes. The polymer matrix can also include a plurality of nitric oxide-donating crosslinking moieties that covalently crosslink polysiloxanes in the plurality of polysiloxanes. The nitric oxide-donating crosslinking moieties can be present in an equimolar amount of covalently attached SNAP is present with respect to the crosslinking agent. For example, the nitric oxide-donating crosslinking moieties can be present in an amount from about 0.1 micromoles to about 0.801 micromoles, from about 0.1 micromoles, about 0.2 micromoles, about 0.3 micromoles, or about 0.35 micromoles or greater per milligram of the polymer matrix. Each of the nitric oxide-donating crosslinking moieties can have a structure according to the formula

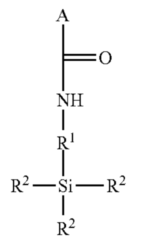

where A is a nitric oxide donor; where $R^1$ is selected from a substituted or unsubstituted $C_1$-$C_{20}$ alkyl, a substituted or unsubstituted $C_1$-$C_{20}$ heteroalkyl, a substituted or unsubstituted $C_2$-$C_{20}$ alkenyl, a substituted or unsubstituted $C_2$-$C_{20}$ heteroalkenyl, a substituted or unsubstituted $C_1$-$C_{20}$ alkoxy, or a substituted or unsubstituted $C_1$-$C_{20}$ heteroalkoxy; and where each occurrence of $R^2$ is independently a substituted or unsubstituted $C_1$-$C_{20}$ alkyl, a substituted or unsubstituted $C_1$-$C_{20}$ heteroalkyl, a substituted or unsubstituted $C_2$-$C_{20}$ alkenyl, a substituted or unsubstituted $C_2$-$C_{20}$ heteroalkenyl, a substituted or unsubstituted $C_1$-$C_{20}$ alkoxy, a substituted or unsubstituted $C_1$-$C_{20}$ heteroalkoxy, or a bond to a polysiloxane in the plurality of polysiloxanes when at least two occurrences of $R^2$ are a bond to a polysiloxane in the plurality of polysiloxanes.

Another aspect of the present disclosure includes a device having at least one surface, wherein the surface comprises a nitric oxide-releasing material as described above.

Another aspect of the present disclosure includes a method of preventing blood clotting or adhesion of a biomaterial to a surface by applying a nitric oxide-releasing material as described above to the surface.

An aspect of the present disclosure also includes a method of preventing biofilm formation on a surface of an article, in which a nitric oxide-releasing material as described above is applied or attached to the surface.

An aspect of the present disclosure also includes a method of making a nitric oxide-releasing material. The method can include crosslinking a plurality of polysiloxanes with a plurality of amine-functionalized crosslinking moieties to produce a crosslinked polymer matrix. Thiolactone can be covalently attached to an amine in the amine-functionalized crosslinking moieties to produce a thiol-functionalized crosslinked polymer matrix. A thiol in the thiol-functionalized crosslinked polymer matrix can be nitrosated to produce the nitric oxide-releasing material.

Other compositions, apparatus, methods, features, and advantages will be or become apparent to one with skill in the art upon examination of the following drawings and detailed description. It is intended that all such additional compositions, apparatus, methods, features and advantages be included within this description, be within the scope of the present disclosure, and be protected by the accompanying claims.

BRIEF DESCRIPTION OF THE DRAWINGS

Further aspects of the present disclosure will be readily appreciated upon review of the detailed description of its various embodiments, described below, when taken in conjunction with the accompanying drawings.

(FIG. 2B) Cumulative NO release over the 125-day testing period was measured and normalized per cm2 of SNAP-PDMS. (FIG. 2C) Representative NO release profile on day 0 from SNAP-PDMS films when placed in PBS with EDTA at 37° C. Error bars represent standard deviation.

FIGS. 6A-6C show hemocompatibility measurements of SNAP-PDMS coated tubing for ECC testing. (FIG. 6A) Time-dependent effects of NO release from the ECC on platelet count over the course of the 4 h study (n=3). (FIG. 6B) Quantification of clot mass obtained from the thrombogenicity chamber. (FIG. 6C) Visual representation of the clotting that occurred in PDMS coated controls (left) and SNAP-PDMS coated circuits (right). P<0.05 was used for comparison. Error bars represent standard deviation.

DETAILED DESCRIPTION

Figure 1:
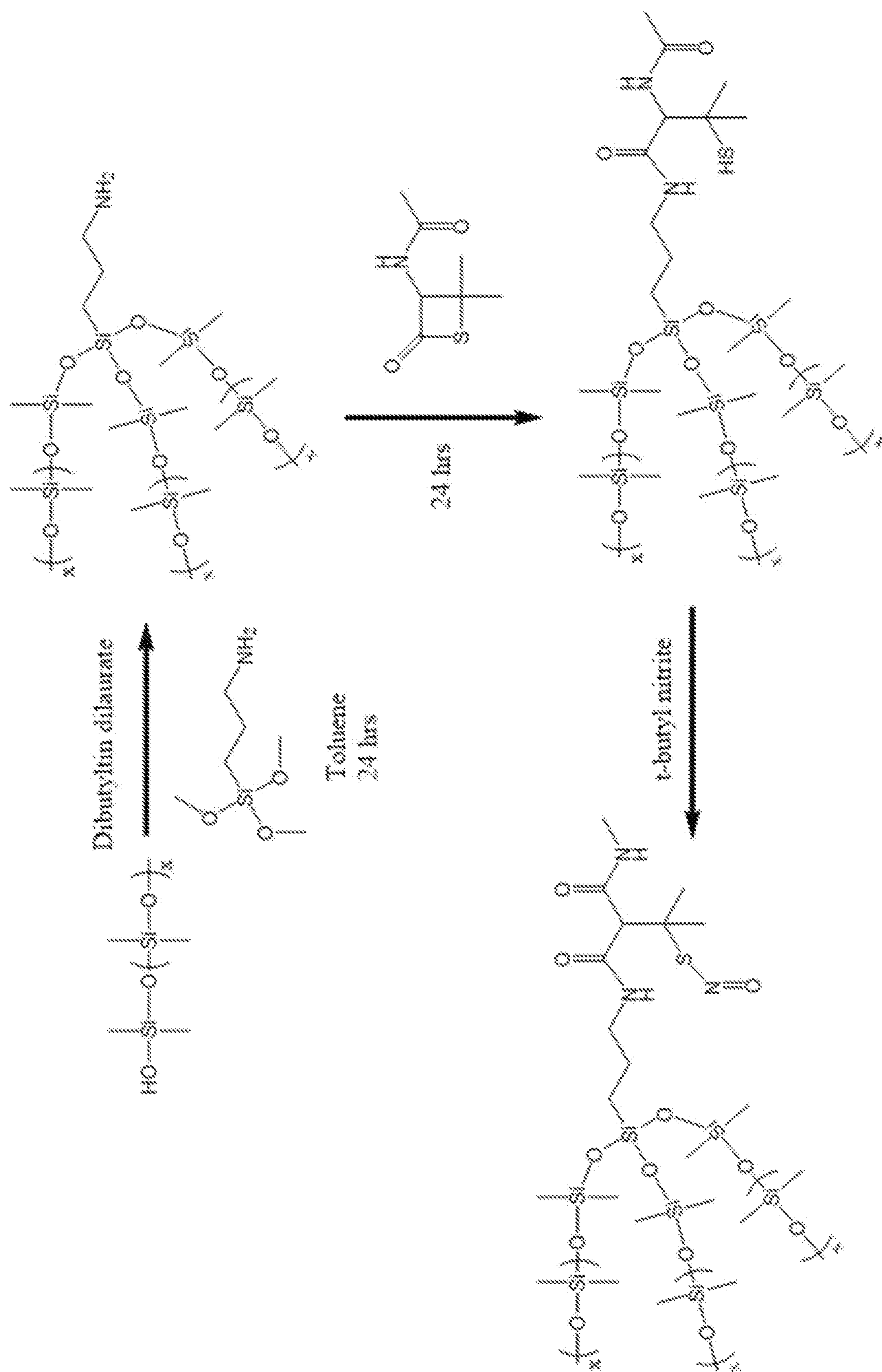
FIG. 1 is a schematic synthetic route for covalently binding the SNAP molecule to hydroxy terminated PDMS polymers.

Herein, the effectiveness of covalently attaching SNAP to PDMS (SNAP-PDMS) as a biocompatible polymer was investigated as a means to ward off unwanted thrombus formation and as a long-term antimicrobial agent. By covalently attaching SNAP to the aminosilane crosslinker in PDMS, its in vitro longevity release capabilities were proven by demonstrating the ability to maintain a stable, unprecedented NO release for over 125 days under physiological conditions. The long-term NO release opens a large array of possibilities such as the fabrication and modification of a variety of silicone rubber based biomedical devices such as blood and urinary catheters, PICC lines, and feeding tubes. In terms of hemocompatibility, SNAP-PDMS was coated on the inner lumen of PDMS tubing used for 4 h ECC experiments to observe thrombus formation and overall platelet count using a rabbit model. In a separate experiment, SNAP-PDMS films were tested for 28 days using a CDC biofilm reactor to demonstrate the polymer's antimicrobial capabilities.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure and to be encompassed by the claims herein.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of nanotechnology, organic chemistry, material science and engineering and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'", where 'x' and 'y' are numerical values, includes "about 'x' to about 'y'".

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups.

In some embodiments, a straight chain or branched chain alkyl has 30 or fewer carbon atoms in its backbone (e.g., $C_1$-$C_{30}$ for straight chains, $C_3$-$C_{30}$ for branched chains), 20 or fewer, 12 or fewer, or 7 or fewer. Likewise, in some embodiments cycloalkyls have from 3-10 carbon atoms in their ring structure, e.g. have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a hosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, having from one to ten carbons, or from one to six carbon atoms in its backbone structure. Likewise, "lower alkenyl" and "lower alkynyl" have similar chain lengths. In embodiments described in the present application, preferred alkyl groups are lower alkyls. In some embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), $-CF_3$, $-CN$ and the like. Cycloalkyls can be substituted in the same manner.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In some embodiments, the "alkylthio" moiety is represented by one of —S-alkyl, —S-alkenyl, and —S-alkynyl. Representative alkylthio groups include methylthio, and ethylthio. The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, and tert-butoxy. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The terms "amine" and "amino" are art-recognized and refer to both unsubstituted and substituted amines, e.g., a moiety that can be represented by the general formula:

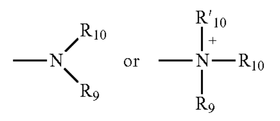

wherein $R_9$, $R_{10}$, and $R'_{10}$ each independently represent a hydrogen, an alkyl, an alkenyl, $-(CH_2)_m-R_8$ or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In some embodiments, only one of $R_9$ or $R_{10}$ can be a carbonyl, e.g., $R_9$, $R_{10}$ and the nitrogen together do not form an imide. In still other embodiments, the term "amine" does not encompass amides, e.g., wherein one of $R_9$ and $R_{10}$ represents a carbonyl. In additional embodiments, $R_9$ and $R_{10}$ (and optionally $R'_{10}$) each independently represent a hydrogen, an alkyl or cycloakly, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of $R_9$ and $R_{10}$ is an alkyl group.

The term "amido" is art-recognized as an amino-substituted carbonyl and includes a moiety that can be represented by the general formula:

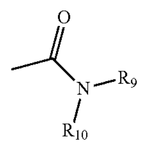

wherein $R_9$ and $R_{10}$ are as defined above.

"Aryl", as used herein, refers to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN; and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined above for "aryl".

The term "aralkyl", as used herein, refers to an alkyl group substituted with an aryl group (e.g., an aromatic or heteroaromatic group).

The term "carbocycle", as used herein, refers to an aromatic or non-aromatic ring in which each atom of the ring is carbon.

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinoxalinyl, quinolizinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, and —CN.

The term "carbonyl" is art-recognized and includes such moieties as can be represented by the general formula:

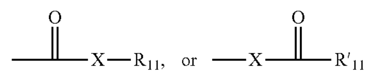

wherein X is a bond or represents an oxygen or a sulfur, and $R_{11}$ represents a hydrogen, an alkyl, a cycloalkyl, an alkenyl, an cycloalkenyl, or an alkynyl, $R'_{11}$ represents a hydrogen, an alkyl, a cycloalkyl, an alkenyl, an cycloalkenyl, or an alkynyl. Where X is an oxygen and $R_{11}$ or $R'_{11}$ is not hydrogen, the formula represents an "ester". Where X is an oxygen and $R_{11}$ is as defined above, the moiety is referred to herein as a carboxyl group, and particularly when $R_{11}$ is a hydrogen, the formula represents a "carboxylic acid". Where X is an oxygen and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R'_{11}$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "heteroatom" as used herein means an atom of any element other than carbon or hydrogen. Examples of heteroatoms include, but are not limited to boron, nitrogen, oxygen, phosphorus, sulfur and selenium. Other heteroatoms include silicon and arsenic.

As used herein, the term "nitro" means $-NO_2$; the term "halogen" designates —F, —Cl, —Br or —I; the term "sulfhydryl" means —SH; the term "hydroxyl" means —OH; and the term "sulfonyl" means $-SO_2-$.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms (for example, 1-14 carbon atoms), and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. The heteroatoms such as nitrogen may have hydrogen substituents and/or any permissible substituents of organic compounds described herein which satisfy the valencies of the heteroatoms.

In various aspects, the substituent is selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone, each of which optionally is substituted with one or more suitable substituents. In some embodiments, the substituent is selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, thioketone, ester, heterocyclyl, —CN, aryl, aryloxy, perhaloalkoxy, aralkoxy, heteroaryl, heteroaryloxy, heteroarylalkyl, heteroaralkoxy, azido, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like. In some embodiments, the substituent is selected from cyano, halogen, hydroxyl, and nitro.

The term "copolymer" as used herein, generally refers to a single polymeric material that is comprised of two or more different monomers. The copolymer can be of any form, such as random, block, graft, etc. The copolymers can have any end-group, including capped or acid end groups.

As used herein, the term "linker" refers to a carbon chain that can contain heteroatoms (e.g., nitrogen, oxygen, sulfur, etc.) and which may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 atoms long. Linkers may be substituted with various substituents including, but not limited to, hydrogen atoms, alkyl, alkenyl, alkynl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, and ureido groups. Those of skill in the art will recognize that each of these groups may in turn be substituted. Examples of linkers include, but are not limited to, pH-sensitive linkers, protease cleavable peptide linkers, nuclease sensitive nucleic acid linkers, lipase sensitive lipid linkers, glycosidase sensitive carbohydrate linkers, hypoxia sensitive linkers, photo-cleavable linkers, heat-labile linkers, enzyme cleavable linkers (e.g., esterase cleavable linker), ultrasound-sensitive linkers, and x-ray cleavable linkers.

Discussion

As described below, the present disclosure provides nitric oxide releasing materials, methods of making nitric oxide releasing materials, and devices including nitric oxide releasing materials. A strategy to improve the biocompatibility in these scenarios can be through the utilization of nitric oxide (NO). Nitric oxide is a free radical molecule produced in the body with a wide range of biological signaling functions. Some of the most notable physiological functions are the prevention of platelet adhesion to vasculature, regulation of blood pressure through vasodilation, and as a method for macrophages to eliminate pathogens via nitrosative stress.[3-4] Knowing these mechanisms has led to the development of NO releasing materials that are capable of mimicking vital endogenous effects under certain conditions. S-nitrosothiols (RSNOs) are a popular class of NO releasing molecules that are produced by the body. Some RSNOs such as S-nitroso-N-acetyl penicillamine (SNAP), S-nitrosoglutathione (GSNO), and S-nitrosocysteine have been incorporated into polymer matrices to create environments with localized and controlled NO release.[5-7] The release mechanism of NO from RSNOs is done by the cleavage of the sulfur-nitrogen bond and is facilitated by either thermal degradation, metal ion catalysis, and/or light. Thermal degradation is one of those most commonly used methods for initiating this release of RSNO-containing materials because in vivo temperatures are able to promote a passive, steady NO release. Diazeniumdiolates are another class of NO-donating compounds that use physiological temperature and pH to passively release large quantities of NO over short periods of time.[8]

The role of NO releasing polymers as a method to prevent thrombus formation has been thoroughly investigated in multiple studies in vivo using both extracorporeal circuit (ECC) and catheter models.[9-14] Since NO has a short half-life, its mode of action demonstrates a more localized effect when suppressing platelet activation. Blood thinners such as heparin have systemic effects within a patient, which can lead to low platelet counts, unwanted internal bleeding, and thrombocytopenia.[15-16] Polymers capable of generating NO are a possible solution to this as they demonstrate a drastic reduction in thrombus formation and platelet adhesion on both ECC and catheter surfaces without having this detrimental systemic effect.

Another common problem with tissue-contacting medical devices is the ongoing risk of infection. A large number of antimicrobial surfaces have been developed with strategies such as incorporating metal or metal oxide nanoparticles like silver[17-19] and copper[20-22] as well as polymeric materials that facilitate the diffusion of certain antibiotics.[23-25] However, these metallic nanoparticles can be cytotoxic to the surrounding tissue in addition to the bacteria being targeted if used in high concentration. Drug-resistant bacteria have also been on the rise, limiting the potential application of antibiotics.[26-27] Antibiotics have also been shown to be ineffective against biofilms, which provide a protective matrix containing proteins and polysaccharides for the bacteria.[28] Controlled levels of nitric oxide from a wide range of nitric oxide donors have been shown to be able to eliminate numerous types of bacterial strains while still demonstrating noncytotoxic effects to surrounding cells.[29-32] This strategy utilizes NO as an antimicrobial agent in a similar manner to the way macrophages employ it to eliminate bacteria and has proven to be effective against antibiotic-resistant strains of bacteria and to disperse biofilms.[33-35] Most NO releasing materials are generally short-lived and cannot be applied to materials or devices that require a long implantation time. The most efficient way to have a long-term NO releasing antimicrobial material is to ensure the covalent attachment of an RSNO to a material. This strategy prevents leaching out of the polymer matrix, which usually yields high bursts of NO over a short period of time and depletion of its NO reservoir. High molecular weight dendrimers have also been synthesized with covalently bound NO donors like RSNO's and diazeniumdiolates and have shown to have a large, controlled NO releasing capacity.[36-37] Using this strategy, synthetics have shown the potential to be stable in vitro platforms for delivering NO to cells over a monitored period of time.[38-39]

Nitric Oxide Releasing Materials and Articles and Methods of Making and Uses Thereof.

In some aspects, a nitric oxide releasing material is provided comprising a polymer matrix, wherein the polymer matrix includes (i) a plurality of polysiloxanes; and (ii) a plurality of nitric oxide-donating crosslinking moieties covalently crosslinking polysiloxanes in the plurality of polysiloxanes; wherein the nitric oxide-donating crosslinking moieties are present in an amount from about 0.1 to about 0.801 micromoles, about 0.1 micromoles, about 0.2 micromoles, about 0.3 micromoles, or about 0.35 micromoles or greater per milligram of the polymer matrix; and wherein each of the nitric oxide-donating crosslinking moieties in the plurality of nitric oxide-donating crosslinking moieties comprises S-nitroso-N-acetyl-penicillamine groups covalently attached thereto.

In some aspects, a nitric oxide releasing material is provided comprising a polymer matrix, wherein the polymer matrix comprises (i) a plurality of polysiloxanes; and (ii) a plurality of nitric oxide-donating crosslinking moieties covalently crosslinking polysiloxanes in the plurality of polysiloxanes; wherein the nitric oxide-donating crosslinking moieties are present in an amount from about 0.1 micromoles, about 0.2 micromoles, about 0.3 micromoles, or about 0.35 micromoles or greater per milligram of the polymer matrix; and wherein each of the nitric oxide-donating crosslinking moieties in the plurality of nitric oxide-donating crosslinking moieties has a structure according to the following formula:

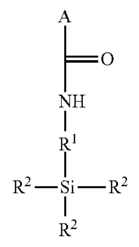

where A is a nitric oxide donor; where $R^1$ is selected from a substituted or unsubstituted $C_1$-$C_{20}$ alkyl, a substituted or unsubstituted $C_1$-$C_{20}$ heteroalkyl, a substituted or unsubstituted $C_2$-$C_{20}$ alkenyl, a substituted or unsubstituted $C_2$-$C_{20}$ heteroalkenyl, a substituted or unsubstituted $C_1$-$C_{20}$ alkoxy, or a substituted or unsubstituted $C_1$-$C_{20}$ heteroalkoxy; where each occurrence of $R^2$ is independently a substituted or unsubstituted $C_1$-$C_{20}$ alkyl, a substituted or unsubstituted $C_1$-$C_{20}$ heteroalkyl, a substituted or unsubstituted $C_2$-$C_{20}$ alkenyl, a substituted or unsubstituted $C_2$-$C_{20}$ heteroalkenyl, a substituted or unsubstituted $C_1$-$C_{20}$ alkoxy, a substituted or unsubstituted $C_1$-$C_{20}$ heteroalkoxy, or a bond to a polysiloxane in the plurality of polysiloxanes wherein at least two occurrences of $R^2$ are a bond to a polysiloxane in the plurality of polysiloxanes.

In some aspects, A is an S-nitrosothiol. In some aspects, the S-nitrosothiol is selected from the group consisting of S-nitroso-N-acetyl-penicillamine, S-nitroso-N-acetyl cysteine, S-nitroso-N-acetyl cysteamine, S-nitrosoglutathione, methyl S-nitrosothioglycolate, and a derivative thereof. In some aspects, the nitric oxide donor (A) is a diazeniumdiolate. In some aspects, the diazeniumdiolate is diazeniumdiolated dibutylhexanediamine or a derivative thereof.

In some aspects, the nitric oxide donor is a diazeniumdiolate. In some aspects, the diazeniumdiolate is diazeniumdiolated dibutylhexanediamine or a derivative thereof.

In some aspects, A has a structure according to the formula $R^4SNO$, where $R^4$ is an amino acid or fragment thereof. In some aspects, $R^1$ is a substituted or unsubstituted $C_1$-$C_{12}$ alkyl or a substituted or unsubstituted $C_1$-$C_{12}$ aminoalkyl. In some aspects, each occurrence of $R^2$ is a bond to a polysiloxane in the plurality of polysiloxanes.

In some aspects, the polysiloxanes in the plurality of polysiloxanes are selected from the group consisting of polydimethylsiloxane, polydiethylsiloxane, polydipropylsiloxane, and polydiphenylsiloxane. In some aspects, the plurality of polysiloxanes have a kinematic viscosity of about 2000 cSt to about 4000 cSt when not crosslinked in the polymer matrix.

In some aspects, an equimolar amount of covalently attached SNAP is present with respect to the crosslinking agent. In some aspects, nitric oxide-donating crosslinking moieties are present in an amount from about 0.1 micromoles to about 0.801 micromoles, about 0.2 micromoles to about 0.801 micromoles, about 0.3 micromoles to about 0.801 micromoles, or about 0.35 micromoles to about 0.801 micromoles per milligram of the crosslinked polymer matrix.

In some aspects, a device is provided having at least one surface, wherein the surface comprises a nitric oxide-releasing material described herein. In some aspects, the device comprises a rubber material having the nitric oxide-releasing material dispersed within the rubber. In some aspects, the rubber is a silicone rubber such as PDMS rubber. In some aspects, the nitric oxide-releasing material is applied to a surface of a substrate. In some aspects, the substrate is selected from a polymer, a metal, and a glass.

In some aspects, the device is a urinary catheter, artificial heart valve, a vascular catheter, a graft, or a stent. In some aspects, the device is intended to contact human blood or tissue. In some aspects, the device is a hemodialysis device or a component thereof. In some aspects, the device is an implantable medical device. In some aspects, the device is an anti-biofilm invoking surface. In some aspects, the device can be tested within a bioreactor as a way to test its anti-biofilm capabilities.

In some aspects, a method is provided for preventing blood clotting or adhesion of a biomaterial to a surface, the method can include applying a nitric oxide-releasing material described herein to the surface.

In some aspects, a method is provided for preventing biofilm formation on a surface of an article, the method comprising applying a nitric oxide-releasing material described herein to the surface.

In some aspects, a method of making a nitric oxide-releasing material is provided, the method comprising: crosslinking a plurality of polysiloxanes with a plurality of amine-functionalized crosslinking moieties to produce a crosslinked polymer matrix; covalently attaching a thiolactone to an amine in the amine-functionalized crosslinking moieties to produce a thiol-functionalized crosslinked polymer matrix; and nitrosating a thiol in the thiol-functionalized crosslinked polymer matrix to produce the nitric oxide-releasing material. In some aspects, the method can further include adding an organic acid to nitrosate the thiol-functionalized crosslinked polymer matrix. Organic acids can include, but are not limited to such as dodecylbenzene sulfonic acid, dinonylnaphthalenedisulfonic acid, 4-octylbenzenesulfonic acid, acetic acid, formic acid, and lactic acid.

In some aspects, the amine-functionalized crosslinking moieties have a structure according to the following formula:

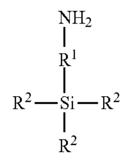

where $R^1$ is selected from a substituted or unsubstituted $C_1$-$C_{20}$ alkyl, a substituted or unsubstituted $C_1$-$C_{20}$ heteroalkyl, a substituted or unsubstituted $C_2$-$C_{20}$ alkenyl, a substituted or unsubstituted $C_2$-$C_{20}$ heteroalkenyl, a substituted or unsubstituted $C_1$-$C_{20}$ alkoxy, or a substituted or unsubstituted $C_1$-$C_{20}$ heteroalkoxy; where each occurrence of $R^2$ is hydroxy or alkoxy.

In some aspects, each occurrence of $R^2$ is a hydroxy, methoxy or ethoxy. In some aspects, $R^1$ is a substituted or unsubstituted $C_1$-$C_{12}$ alkyl or a substituted or unsubstituted $C_1$-$C_{12}$ aminoalkyl. In some aspects, the thiolactone has a structure according to the following formula:

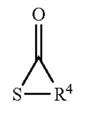

where $R^4$ is a substituted or unsubstituted $C_1$-$C_{12}$ alkyl.

In some aspects, the thiolactone has a structure according to the following formula:

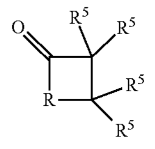

where each occurrence of $R^5$ is independently a hydrogen, a hydroxyl, a substituted or unsubstituted $C_1$-$C_6$ alkyl, substituted or unsubstituted $C_1$-$C_6$ heteroalkyl, a substituted or unsubstituted $C_2$-$C_6$ alkenyl, a substituted or unsubstituted $C_2$-$C_6$ heteroalkenyl, a substituted or unsubstituted $C_1$-$C_6$ alkoxy, or a substituted or unsubstituted $C_1$-$C_6$ heteroalkoxy.

In some aspects, the thiolactone is N-acetyl-D-penicillamine or a derivative thereof. In some aspects, the thiolactone is selected from the group consisting of N-Acetylcysteine thiolactone, N-Acetyl-homocysteine thiolactone, Homocysteine thiolactone, Butyryl-homocysteine thiolactone.

EXAMPLES

Now having described the embodiments of the present disclosure, in general, the following Examples describe some additional embodiments of the present disclosure.

While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1. Achieving Long-Term Thromboresistant and Antimicrobial Silicone Via Covalently Immobilized S-Nitroso-N-Acetylpenicillamine (SNAP) that Exhibits 4 Months of Sustained Nitric Oxide Release

Materials and Methods

Materials

N-Acetyl-D-penicillamine (NAP), hydroxy terminated poly(dimethylsiloxane) 2550-3570 cSt (PDMS), (3-aminopropyl) trimethoxysilane, dibutyltin dilaurate, toluene, chloroform, pyridine, tert-butyl nitrite, acetic anhydride, ethylenediaminetetraacetic acid (EDTA), concentrated hydrochloric acid (HCl), 1,4,8,11-tetraazacyclotetradecane (cyclam), anhydrous magnesium sulfate, and hexanes were purchased from Sigma Aldrich (St. Louis, MO). Trypsin-EDTA and Cell Counting Kit-8 (CCK-8) was purchased from Sigma-Aldrich (St. Louis, MO). The antibiotic Penicillin-Streptomycin (Pen-Strep) and fetal bovine serum (FBS) were obtained from Gibco-Life Technologies (Grand Island, NY). The bacterial strain *Staphylococcus aureus* (ATCC 5538) and mouse 3T3 cells (ATCC 1658) were originally obtained from American Type Culture Collection.

Synthesis of NAP-Thiolactone

Thiolactone self-protected NAP was synthesized using the established protocol developed by Moynihan and Robert.[40] Briefly, 5 g of NAP was dissolved in 10 ml of pyridine in a round bottom flask while a separate vial containing 10 mL of pyridine and 10 ml of acetic anhydride was made. Both solutions were allowed to chill in an ice bath for 1 h before being combined and allowed to stir for 24 hrs. The solution was then rotary evaporated at 60° C. until all of the pyridine is evaporated and only small amount of a viscous, orange solution remains. The remaining solution was then dissolved in 20 mL of chloroform and washed and extracted three times with equal volume quantities of 1M HCl. The organic layer was then dried over anhydrous magnesium sulfate and filtered. The chloroform is then removed under vacuum at room temperature and the resulting solid is washed and filtered with hexanes. The collected pale, white-yellow solid is then dried overnight at room temperature before being stored at 5° C. (1.16 g).

Synthesis of SNAP-PDMS

SNAP-PDMS was synthesized by slightly modifying a protocol by Frost et al.[41] A schematic is shown in FIG. 1, where initially 1.6 g of hydroxy terminated PDMS was dissolved in 8 mL of toluene. In a separate vial, 0.3 g of (3-aminopropyl) trimethoxysilane (1.67 mmol) and 2.4 mg of dibutyltin dilaurate were dissolved in 2 mL of toluene. The two solutions were then combined and thoroughly mixed and allowed to stir overnight. A slight excess (300 mg, 1.73 mmol) of NAP-thiolactone with respect to the crosslinking agent was dissolved in the crosslinked PDMS solution and then allowed to stir for 24 hrs. Nitrosation of the formed NAP-PDMS was done by adding t-butyl nitrite. T-butyl nitrite was first chelated of any copper contaminants by vortexing it with an equal volume amount of 20 mM cyclam solution and repeated three times. The organic t-butyl nitrite layer is then separated into an amber vial and stored at 5° C. 300 μL of t-butyl nitrite is then added to 3 mL of NAP-PDMS to form a dark green, SNAP-PDMS solution. The nitrosated solution was then placed into a 2.54 cm diameter Teflon ring, protected from light, and left to air dry overnight.

In order to enhance the nitrosation efficiency, an organic acid can be added after nitrosation. Organic acids can include, but are not limited to such as dodecylbenzene sulfonic acid, dinonylnaphthalenedisulfonic acid, 4-octylbenzenesulfonic acid, acetic acid, formic acid, lactic acid. Example concentrations can be about 50 microliters of acid per 3 mL of NAP-PDMS solution, although other ratios and concentrations can be envisioned by one of ordinary skill in the art. In the present examples, the efficiency gains of the nitrosation could be visually detected via a color change to a darker green, indicating the formation of more SNAP functional groups.

Nitric Oxide Detection

NO release from the SNAP-PDMS polymers was directly measured in real time via chemiluminescence using a Sievers Nitric Oxide Analyzer (NOA) model 280i (Boulder, CO). Films were tested by immersing them in 0.01M PBS containing EDTA at 37° C. inside of an amber reaction chamber. A nitrogen bubbler was then placed in the solution containing the polymer at a flow rate of 200 mL min-1 to carry any NO being emitted to the NOA.

SNAP Leaching Assay

Comparison of leaching between covalent bound SNAP-PDMS and blended SNAP PDMS was quantified by a Genesys 10S UV-Vis spectrophotometer (ThermoFisher, Waltham, MA). The characteristic S-nitroso bond seen in RSNO's shows absorbance maxima at 340 and 590 nm.[42-43] Diffusion of SNAP from the PDMS was done by soaking SNAP-PDMS and SNAP blended PDMS films for varying amounts of time in 0.01M PBS (pH=7.4) with 100 μm EDTA to ensure there is little catalytic metal ion interaction in the buffer. Blended SNAP in PDMS and covalent bound SNAP-PDMS were both tested with and without a topcoat of PDMS. Film were measured and incubated in PBS with EDTA at room temperature while being protected from light to preserve the SNAP leaching values over the course of the study. Measured aliquots of the PBS solution were placed into cuvettes to be measured at 340 nm.

Bacterial Adhesion Assay

The ability of SNAP-PDMS to prevent bacterial binding and growth on the polymeric surface was tested in vitro for 3, 14, and 28 days in a continuous flow CDC bioreactor (BioSurface Technologies) against *Staphylococcus aureus* (*S. aureus*). The use of CDC bioreactor provides a highly favorable environment for bacterial growth through a continuous supply of nutrients for the formation of a biofilm on the polymeric surface to test the long-term performance of the polymer. A single isolated colony of the bacterial strain (*S. aureus*) from a pregrown culture was incubated overnight in LB medium for 14 h at 150 rpm at 37° C. After 14 h, optical density (O.D) of the liquid suspension of bacteria was measured at 600 nm (OD600) using a UV-vis spectrophotometer as recommended by earlier reports.[44] Before being tested, the sample films (SNAP-PDMS and control PDMS, n=3 for each time point) were sterilized by UV irradiation for 30 mins under a Biosafety Cabinet (Thermo Scientific 1300 A2) and fitted inside the CDC bioreactor. Prior to use, the CDC bioreactor was sterilized using high pressure saturated steam for 30 min at 121° C. in an autoclave. The CDC bioreactor (working volume 1000 mL) with 400 mL of LB medium (2 g $L^{-1}$) was inoculated with the bacterial culture in a manner that the final OD600 falls in the range of $10^7$-$10^9$ CFU $mL^{-1}$ to simulate chronic infection conditions. The CDC bioreactor on one end was connected to a feed bottle having a continuous supply of sterile LB medium (2 g $L^{-1}$) and to a sealed container to collect the wash out in a sterile manner on the other end. After 3, 14, and 28 days, the films (controls and tests) were removed and gently rinsed with phosphate buffer saline, pH 7.4 (PBS) to get rid of any loosely bound bacteria. The rinsed films were then transferred to a 15 ml tube with 2 mL sterile PBS and homogenized for 60 sec using an OmniTip homogenizer. The shear force from the homogenizer tip ensured the transfer of the bound bacterial strains from the tubing to the PBS solution. Thereafter, serial dilution ($10^{-1}$ to $10^{-5}$) were made using sterile PBS and bacterial strains were plated on different Petri-dishes solid LB-agar medium using an L-spreader. After adjusting the dilution factor, the volume of bacteria culture plate, starting culture volume, and other variables, the antimicrobial efficacy of the SNAP-PDMS films was compared to the control films as follows.

$$\text{Bacterial Inhibition (\%)} = \frac{\left(\frac{CFU}{cm^2}\text{ in control samples} - \frac{CFU}{cm^2}\text{ in test samples}\right)\times 100}{\frac{CFU}{cm^2}\text{ in control samples}}$$

In Vitro Cell Cytotoxicity

Cell cytotoxicity was performed on SNAP-PDMS films on 3T3 mouse fibroblast cells (ATCC-1658) per the ISO 10993 standard. The Cell Counting Kit-8 (CCK-8) protocol was followed which uses WST-8 dye [2-(2-methoxy-4-nitrophenyl)-3-(4-nitrophenyl)-5-(2,4-disulfophenyl)-2H-tetrazolium monosodium salt]. WST-8 is enzymatically reduced in live cells to produce formazan, which is detectable at 450 nm. This measurement is then used to directly quantify the number of living cells while not requiring the killing of the cells.

Mouse fibroblast cells were cultured on 75 $cm^2$ T-flasks in DMEM containing 4.5 g $L^{-1}$ glucose and L-glutamine, 10% FBS, and 1% penicillin-streptomycin at 37° C. under a humidified atmosphere with 5% $CO_2$. Once confluency reached 90%, cells were trypsinized (0.18% trypsin and 5 mM EDTA) and seeded in 96-well plates at a concentration of 5000 cells $mL^{-1}$. Simultaneously, leachates from control PDMS and SNAP-PDMS films were obtained by soaking the films (n=3) in DMEM medium (1 mL of medium per 1 mg of polymer film) and incubated for 24 h at 37° C. The films were then removed from the solution and discarded while the DMEM containing extracts was kept at 4° C. prior to being used in the cell culture experiments.

The previously made suspension of cells (5000 cells $mL^{-1}$) were inoculated in a 96 well plate (100 μL per well) to be used for cytotoxicity studies. The 96 well plate was then incubated at 37° C., 5% $CO_2$ for 24 h before the leachates were added (10 μL) to each well. The plate was then incubated for another 24 h to allow the possible toxic leachates to impact the cells. Each well then had 10 μL of CCK-8 solution added and was incubated for another 3 h. The absorbance was measured at 450 nm and a comparison was made between the cells with and without leachate to calculate relative cell viability. Results were reported as a percentage of cell viability using the following equation.

$$\text{Relative Cell Viability (\%)} = \frac{\text{Absorbance of the test samples}}{\text{Absorbance of the control samples}}\times 100$$

Extracorporeal Circuit Preparation

The ECC loop configuration was used as previously described.[45-46] Briefly, the fully constructed ECC loops consisted of 16-gauge and 14-gauge IV polyurethane angiocatheters (Kendall Monoject Tyco Healthcare Mansfield, MA), two 16 cm lengths of ¼ inch inner diameter (ID) silicone rubber (SR) tubing, and one 8 cm length of ⅜ inch SR tubing to create a thrombogenicity chamber to promote stagnant and recirculating regions of blood. The angiocatheters were coated only a single time with a more dilute solution of SNAP-PDMS (80 mg $mL^{-1}$). The SR control ECC loops consisted of the SR tubing (no SNAP) and angiocatheters coated with PDMS at the same concentrations as the SNAP-PDMS ECC loops. All ECC loops pieces were assembled together using a solution of 80 mg $mL^{-1}$ PDMS in toluene. The tubing and coating solutions were protected from light throughout this process to minimize the loss of NO. The ECC loops dried under ambient conditions for 48 h followed by vacuum drying for 24 h. The ECC loops were soaked in saline solution for 1 h and this solution was discarded immediately prior to the rabbit experiment. Small sections of the tubing were used to examine the NO release before and after the study.

Rabbit ECC Model

A previously used rabbit ECC model was used to evaluate the hemocompatibility of the SNAP-PDMS coated tubing.[45-47] All animal handling and surgical procedures were approved by the University of Georgia Institutional Animal Care and Use Committee. Over the course of the study, 8 New Zealand white male rabbits (2.5-3.5 kg, Charles River) were used. All rabbits were anesthetized using intramuscular injections of ketamine (7 mg $kg^{-1}$), acepromazine (0.01 mg $kg^{-1}$), midazolam (0.1 mg $kg^{-1}$), and buprenorphine (0.03 mg $kg^{-1}$). Isoflurane gas was used as a maintenance anesthesia in 100% oxygen, delivered via tracheotomy at an inhalation rate of 1-3%. Anesthesia was then maintained through mechanical ventilation of isoflurane in 100% oxygen (from 0.5-1.5%) at a rate of 12 breaths per minute and a tidal volume of 10-15 mL $kg^{-1}$ (Hallowell EMC, Pittsfield, MA 01201). Blood pressure was carefully monitored using a Doppler ultrasonic flow probe (Parks Medical, Las Vegas, NV 89119). Continuous ECG and heart rate were carefully monitored using a multiparameter monitor (Grady Medical, Los Angeles, CA). To aid in the maintenance of blood pressure stability, Lactated Ringer's were administered at a rate of 10 mL $kg^{-1}$ $h^{-1}$ via catheterization of the ear vein. Body temperature was measured via a rectal probe and maintained at 38° C. using a warm water heating blanket and forced air heater. Before the ECC experiment began, blood samples were collected to obtain baseline measurements.

The ECC was primed with 0.9% NaCl and then clamped and placed into position by cannulating the right carotid artery and left jugular vein. Flow through the ECC was then initiated by unclamping both ends to allow blood to move freely through the loop and monitored using an ultrasonic flow probe and flow meter (Transonic 400 Ithaca, NY). Clotting of the ECC loop was defined as when the flow rate reached 0 mL $min^{-1}$ and remained at no flow for 5 min. After clotting occurred or after the 4 h time period had been reached, the ECC loop was clamped, removed from the animal, and rinsed with 60 mL of saline to observe any clotting. Any clots that were formed in the ECC loop were collected, weighed, and stored in formalin. All animals were not systemically anticoagulated during the experiments.

Whole blood samples were drawn from the femoral artery by direct catheterization and collected for analysis of complete blood count using a Heska Element HT5 Hematology Analyzer (CBC; including platelet count). Blood samples were collected every hour for 4 h following the initiation of flow through the ECC, where 1 mL of blood was drawn before each sample was collected. Complete blood count was performed using an impedance counter (CBC-Diff, Heska Corp. Loveland, CO).

Statistical Analysis

Data taken were expressed as mean±standard deviation. Statistical analysis was carried out using a student's t-test with SAS JMP software. P value<0.05 was considered statistically significant for all data throughout the study.

Results and Discussion

Nitric Oxide Release Measurements and Characterization

Figures 2A, 2B, 2C:
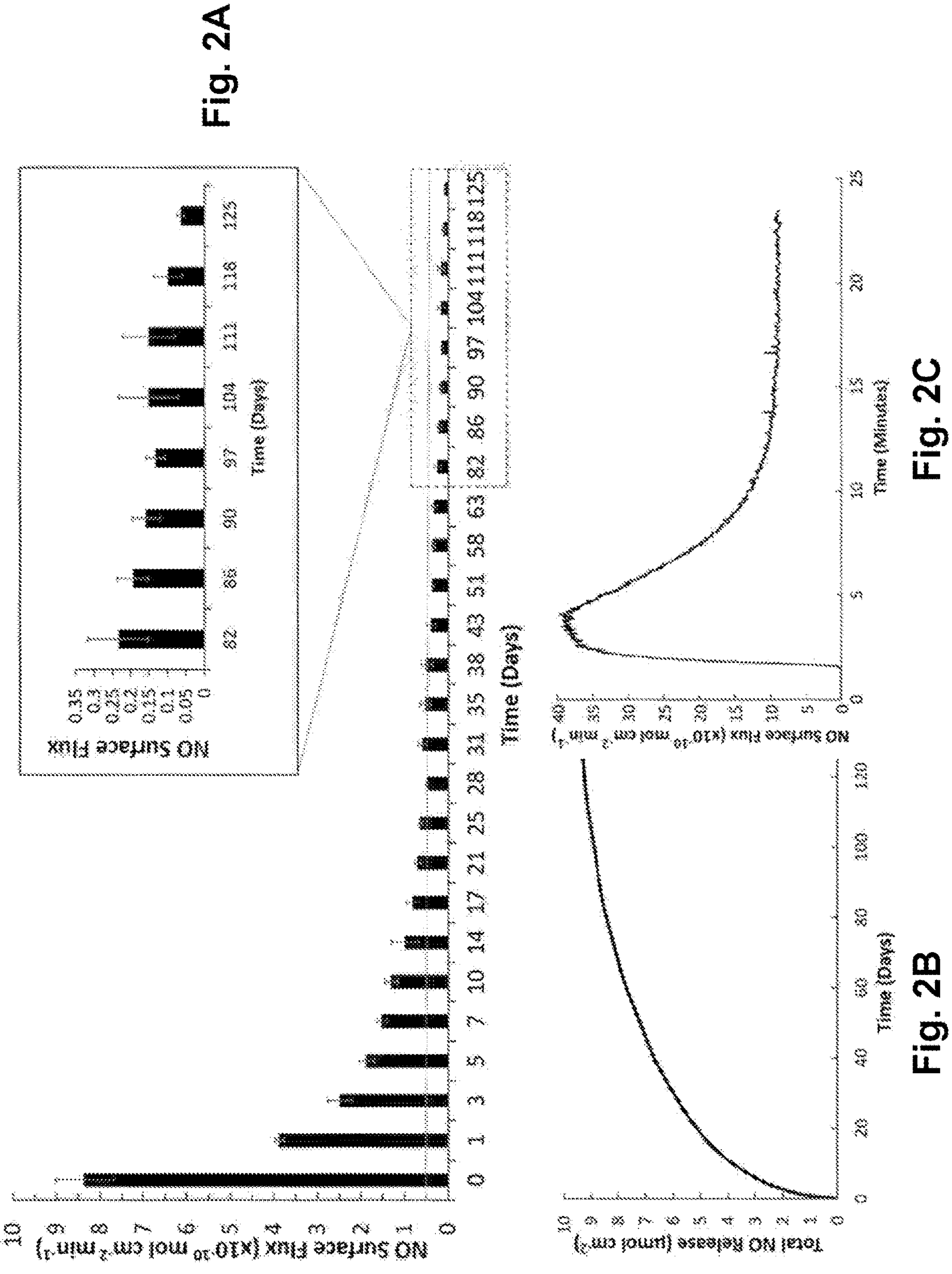
FIGS. 2A-2C show nitric oxide releasing kinetics of SNAP-PDMS films where (FIG. 2A) continuous NO release flux measurements were taken on specified days while storing the films in PBS with EDTA at 37° C. (n=4). The green line represents the minimum physiological level of NO flux (0.5×10-10 mol cm-2 min-1).

Release of NO from SNAP-PDMS films was measured in real time using a chemiluminescence nitric oxide analyzer. Samples were tested in amber reaction vessels containing 0.01M PBS with EDTA at 37° C. using a nitrogen bubbler and sweep gas at a combined flowrate of 200 mL min-1. Up to 125 days of NO testing was done on SNAP-PDMS films while being incubated under the same testing conditions for the entire duration. By the end of the study, the films still possessed the characteristic green color seen with tertiary RSNO modified materials, indicating there is still a reservoir of NO to be emitted. FIGS. 2A-2C show a general overview of the NO release kinetics of the films during the study. A summary of the flux being emitted at designated time points is shown in FIG. 2A, where the PBS used to incubate the films is changed regularly. By the end of the testing period, the films were not completely exhausted and still releasing an NO flux of $0.1\times10^{-10}$ mol $cm^{-2}$ $min^{-1}$. FIG. 2B shows the cumulative NO release that was calculated over this 125-day testing period and demonstrates the overall large NO storage ability the material holds, while FIG. 2C gives the initial release profile when first placed in PBS on day 0. Films were weighed and measured before testing and found to have a SNAP loading capacity of 0.379±0.016 μmol $mg^{-1}$ using UV-VIS. After day 125, there is still 18% of the remaining covalently attached SNAP as the cumulative NO release was normalized to 0.311±0.009 μmol $mg^{-1}$. This duration of release under physiological conditions exceeds expectations when compared to other popular NO releasing polymers that contain non-tethered RSNO's, which normally only release NO under these conditions for a matter of hours or days. This is often due to leaching of the NO donor out of the polymer matrix. Leaching is a challenge for non-covalently attached drugs, and a topcoat of polymer is often used as a preventative measure. However, this method only delays the release of blended components for a few days, limiting the potential applications for materials that require long-lasting NO release.

Silicone rubber tubing containing coats of SNAP-PDMS was also tested for NO release for 4 h to simulate the release seen during the in vivo ECC tests. Three coats of SNAP-PDMS in toluene (160 mg $mL^{-1}$) were cast on the inner lumen of the SR tubing by completely filling the tubing with the solution and draining it, then allowing 1 h to dry between each coat. Between each drying step most of the excess SNAP-PDMS solution was removed from the tubing. This is primarily done to minimize the unevenness of each polymer layer within the lumen of the tubing to give a uniform NO release throughout the entire circuit during testing. Before the ECC experiments, the tubing was left to vacuum dry at room temperature for 24 h to ensure any remaining solvent was properly evaporated. Nitric oxide release was also measured after in vivo ECC testing to ensure the flux was consistent with the previous in vitro NOA testing, releasing an NO flux of $8.15\pm1.68\times10^{-10}$ mol $cm^{-2}$ $min^{-1}$, while $8.35\pm0.666\times10^{-10}$ mol $cm^{-2}$ $min^{-1}$ was measured before testing.

Measurements of SNAP Leachates

An important distinctive trait with SNAP-PDMS is not having the need for a topcoat to prevent any leaching when placing it in any aqueous environments, cutting down the processing time and allowing the application of extremely thin coats of polymer to a surface. However, topcoats of silicone rubber based materials can further decrease the amount of water uptake into the films along with preventing diffusion of certain ions. This could further extend its longevity by only allowing heat as the method for NO release but lowering the overall NO flux as a result. As shown in the initial NO release profile seen in FIG. 2C, NO release from SNAP-PDMS was able to stabilize in under 15 minutes without the presence of a topcoat. Materials containing loosely bound NO donors often have an initial release that is extremely high to the point where it can be cytotoxic towards surrounding cells. There can also be occurrences where it takes a long time for the materials to maintain a level flux due to this constant leaching of the NO donor. This can be difficult when trying to pinpoint an exact flux of NO being emitted from a material over the duration of a study. When comparing the initial NO releasing trend of SNAP-PDMS to these types of polymers, this burst release is much lower in duration. Most of the prior materials require a pre-incubation period in PBS for 24 hr to ensure this burst effect is not as severe, while this is not needed for the SNAP-PDMS of the present disclosure.

A key factor in determining the longevity of RSNO's under physiological conditions is how quickly the donor is leached into the surrounding environment. By covalently attaching SNAP directly to the PDMS, the amount of leaching is significantly reduced when compared to blending it within the polymer. In the past, a common preventative measure to keep blended SNAP within the polymer matrix is to apply a hydrophobic topcoat.[12] However, even though a noticeable reduction in SNAP leaching is seen in the films using this strategy, the leaching is still much greater than what is seen with the covalently bound SNAP-PDMS.

Figure 3:
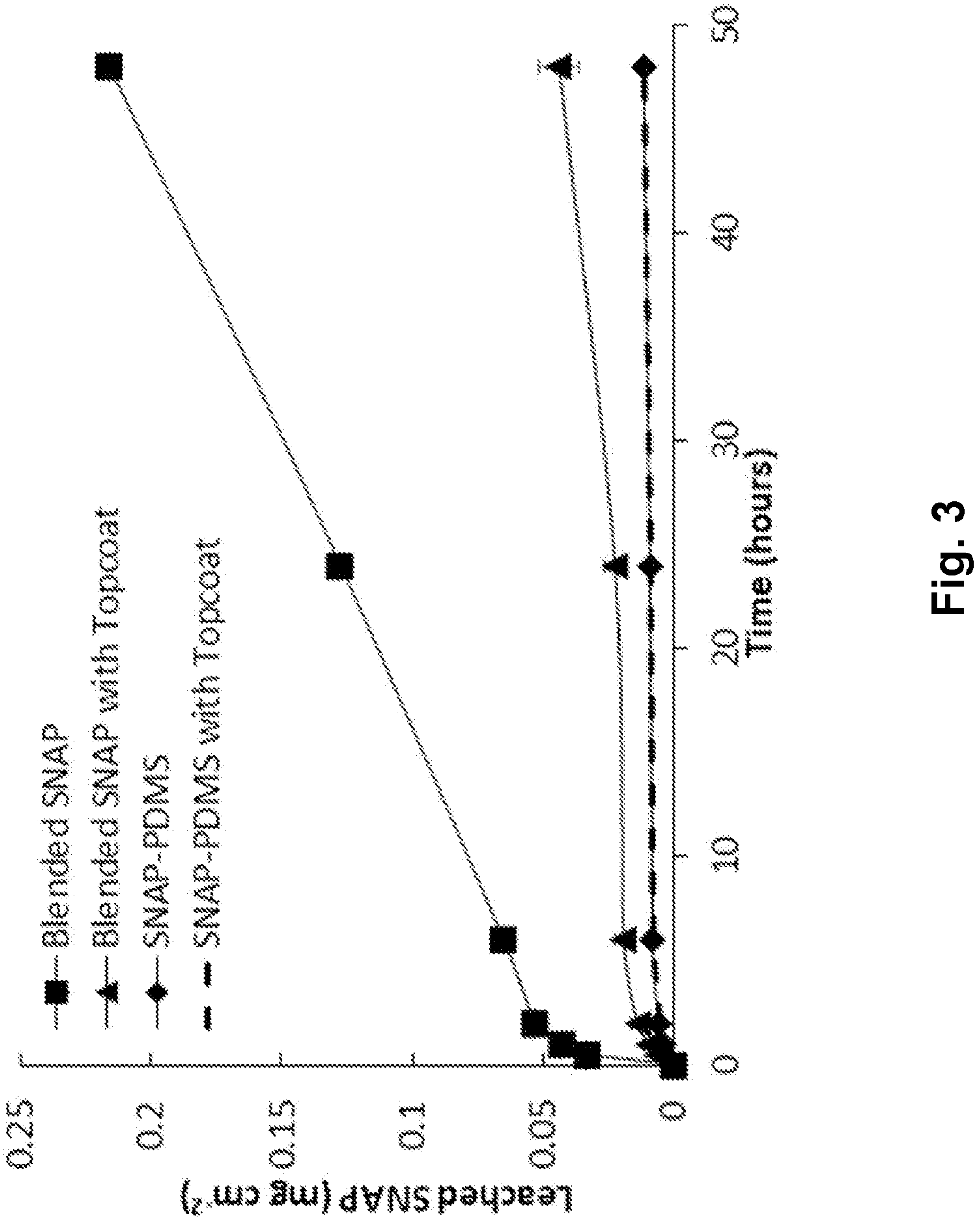
FIG. 3 is a graph of the cumulative leaching of SNAP into PBS from SNAP blended PDMS and covalent bound SNAP-PDMS films with and without a topcoat over the course of 48 hours (n=3). P<0.05 were used for comparison. Error bars represent standard deviation.

Quantification of the amount of leaching seen by the films was observed using UV-Vis absorbance spectroscopy at 340 nm. Over the course of a 48 h period, while being kept at room temperature and protected from light, absorbance was periodically checked from the solutions containing the possible leached SNAP and the trends for each material is shown in FIG. 3. The same solution was used for each testing period so that the cumulative leaching could be calculated for the initial 24 h and a new batch of PBS was used for the following 24 h. After 48 h of soaking the SNAP-PDMS films in PBS at room temperature, little leaching (<0.015 mg $cm^{-1}$) was detected from the SNAP-PDMS films while continuous leaching was seen from the films with the blended SNAP. Even with a protective topcoat, there is still an increasing trend in the amount of leached SNAP from the blended films. This is also visibly verified over the course of the study, as the characteristic green color seen with non-covalent bound SNAP based materials was quickly diminishing. Virtually no difference was detected in the amount of leachates from the SNAP- PDMS with and without a topcoat. Due to the chemistry from the NAP-thiolactone attachment to the aminosilane crosslinker within the PDMS, the only free thiol groups capable of being nitrosated in the PDMS will be covalently bound as any unreacted NAP-thiolactone will remain in its ring structure, preventing it from forming unbound SNAP. There was only a minor increase seen in the initial 6 h of measuring for the SNAP-PDMS films, while the amount of cumulative leachates beyond this timepoint remains almost constant for the duration of the study.

Long Term Inhibition of Bacteria on SNAP-PDMS

Implants are prone to infection due to their surface characteristics along with failure to maintain sterile conditions during medical practices. For instance, catheters are susceptible to infection as they stay implanted for long periods of time. These infections reduce the life time of the device and often need to be replaced before it becomes life threatening. Thus, biomedical device related infections not only add to the suffering of the patient but also increases the overall cost of the healthcare due to prolonged hospital stay. It is important to have long-term antimicrobial strategies so that these types of medical complications can be prevented. The two main parameters by which bacterial adhesion and growth are supported is by the surface roughness of the material and the efficacy of the bactericidal agent being released. Nitric oxide-releasing materials have been proven to greatly reduce bacterial activity, but most of these tests are only done for very short time frames.[44, 48-51] In this study, SNAP-PDMS films were incubated with *S. aureus* in a CDC bioreactor and their antibacterial potential was observed at day 3, 14, and 28, while a separate 24 h study was performed on films that had previously been releasing NO for 125 days continuously. *Staphylococcus aureus* is among one of the major players of hospital-acquired infection which causes biofilm formation on the polymeric surface which renders antibiotics ineffective against it.

Figure 4:
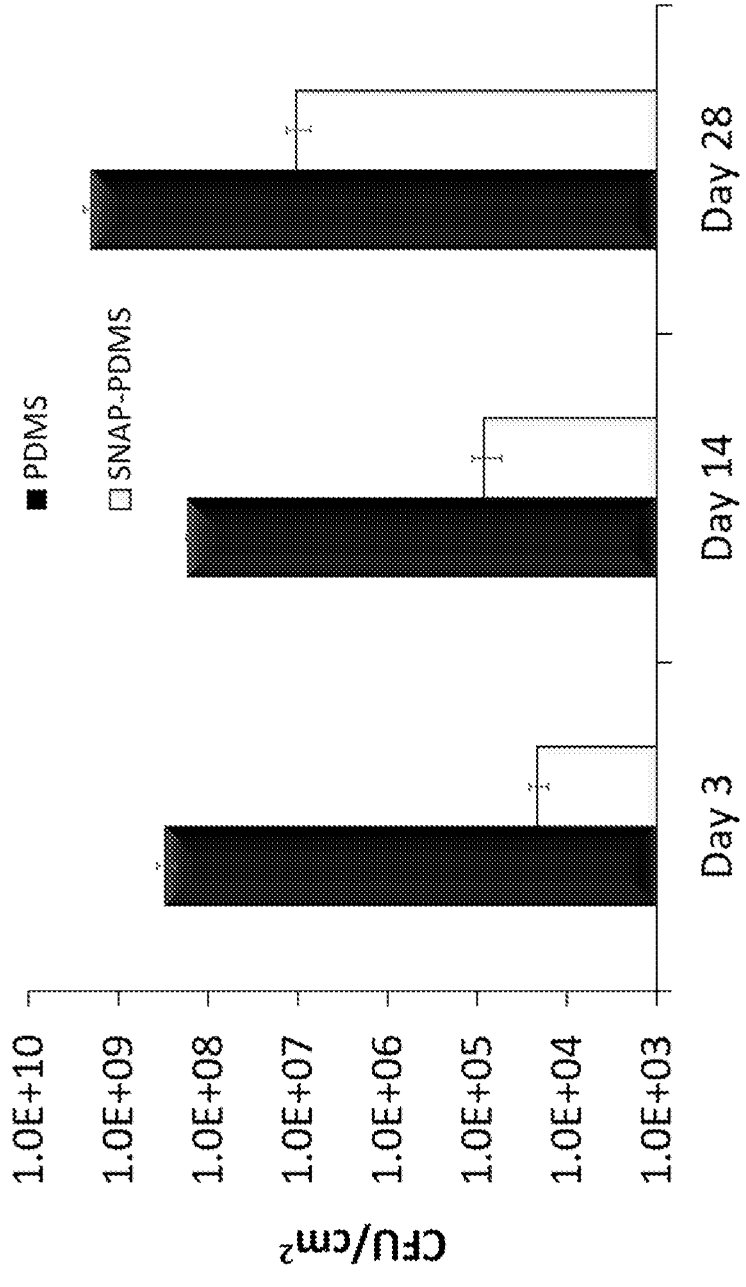
FIG. 4 is a bar graph of the long term antimicrobial ability of *S. aureus* adhesion to SNAP-PDMS. Bacterial adhesion in 28-day bioreactor study on control PDMS and SNAP-PDMS films (n=3 per timepoint), showing approximately a 4, 3, and 2 log reduction in bacterial adhesion by days 3, 14, and 28 respectively. P<0.05 was used for comparison between groups. Error bars represent standard deviation.

The bioreactor used is able to provide a shear force to the films with a constant supply of nutrients to the bacteria to simulate a highly favorable infectious environment seen in vivo.[52] SNAP-PDMS and control PDMS films were placed in CDC bioreactors containing *S. aureus* over a period of 28 days. A constant supply of nutrients (LB Broth, 0.5 g $L^{-1}$) was fed into the bioreactors at a flow rate of 100 mL $hr^{-1}$ while keeping the bioreactor at 37° C. with an agitator speed of 100 rpm. Films (n=3 for each time point) were then taken out at their designated time point: on days 3, 14, and 28. After taking out the films from the bioreactors, they were gently rinsed of any loosely bound bacteria and homogenized in sterile PBS solution with the help of a sonicator (Omni International TH) to detach the bound bacteria from the film. Serial dilutions ($10^{-1}$ to $10^{-5}$) were made and the bacterial suspension in PBS was plated in pre-made LB agar plates (40 mg $mL^{-1}$). The colony forming units per surface area of the SNAP-PDMS films were counted and compared with the control samples and are shown in FIG. 4. A significant reduction in the amount of viable *S. aureus* attachment to the SNAP-PDMS films was observed at all time points. The maximum reduction was observed at the initial time points of 3 and 14 days due to the high flux of NO being emitted from the SNAP-PDMS at these times, demonstrated over 4-log reduction at day 3 and 3-log reduction by day 14. Even after 28 days when the NO release begins to diminish, there is still a 2-log reduction in viable bacteria to the SNAP-PDMS films. Exact values over the course of the bioreactor study are shown in Table 1.

TABLE 1

Nitric oxide flux before and after bioreactor study with colony forming unit (CFU) counts at specified time points.

| | NO Flux$_{(initial)}$ ($\times 10^{-10}$ mol $cm^{-2}$ $sec^{-1}$) | NO Flux$_{(28\ d)}$ ($\times 10^{-10}$ mol $cm^{-2}$ $sec^{-1}$) | CFU$_{(3\ d)}$ | CFU$_{(14\ d)}$ | CFU$_{(28\ d)}$ |
|---|---|---|---|---|---|
| PDMS | — | — | $3.05 \times 10^8 \pm 7.31 \times 10^7$ | $1.72 \times 10^8 \pm 1.20 \times 10^6$ | $2.05 \times 10^9 \pm 3.90 \times 10^8$ |
| SNAP-PDMS | 8.35 ± 0.666 | 1.01 ± 0.120 | $2.11 \times 10^4 \pm 5.09 \times 10^3$ | $8.38 \times 10^4 \pm 3.01 \times 10^4$ | $1.04 \times 10^7 \pm 3.05 \times 10^6$ |

Finally, the residual NO flux after the bioreactor study was observed to extrapolate how effective the films would be beyond the 28-day testing period. It was found that even after 28 days of bacteria killing, SNAP-PDMS films were still releasing an NO flux of $1.01 \pm 0.120 \times 10^{-10}$ mol $min^{-1}$ $cm^{-2}$, proving that there were still potential antimicrobial properties to be utilized. This level of NO is higher than what was seen with in vitro testing for the films in PBS after 28 days shown previously in FIG. 2A where only approximately $0.5 \times 10^{-10}$ mol $min^{-1}$ $cm^{-2}$ was still being emitted. Theoretically, this discrepancy could be due to a few factors that differ between keeping the films in a bioreactor versus PBS. Layers of dead bacteria could be forming on the surface of the polymer films, artificially creating a biological "topcoat" that slows the release of NO after a period of time. Since the films were homogenized and sonicated after testing to remove any remaining bacteria biofilm, it was not possible to prove this theory after the bioreactor study. Another possibility is that the salinity content in the broth was much lower than the PBS. One of the main methods for facilitating NO release for RSNO's is through catalytic based ionic interaction to break the sulfur-nitrogen bond.[42] Lower ion content would then cause a slower release profile over the 28 days, eventually leveling off at a higher flux by day 28 as seen in the data.

Figure 5:
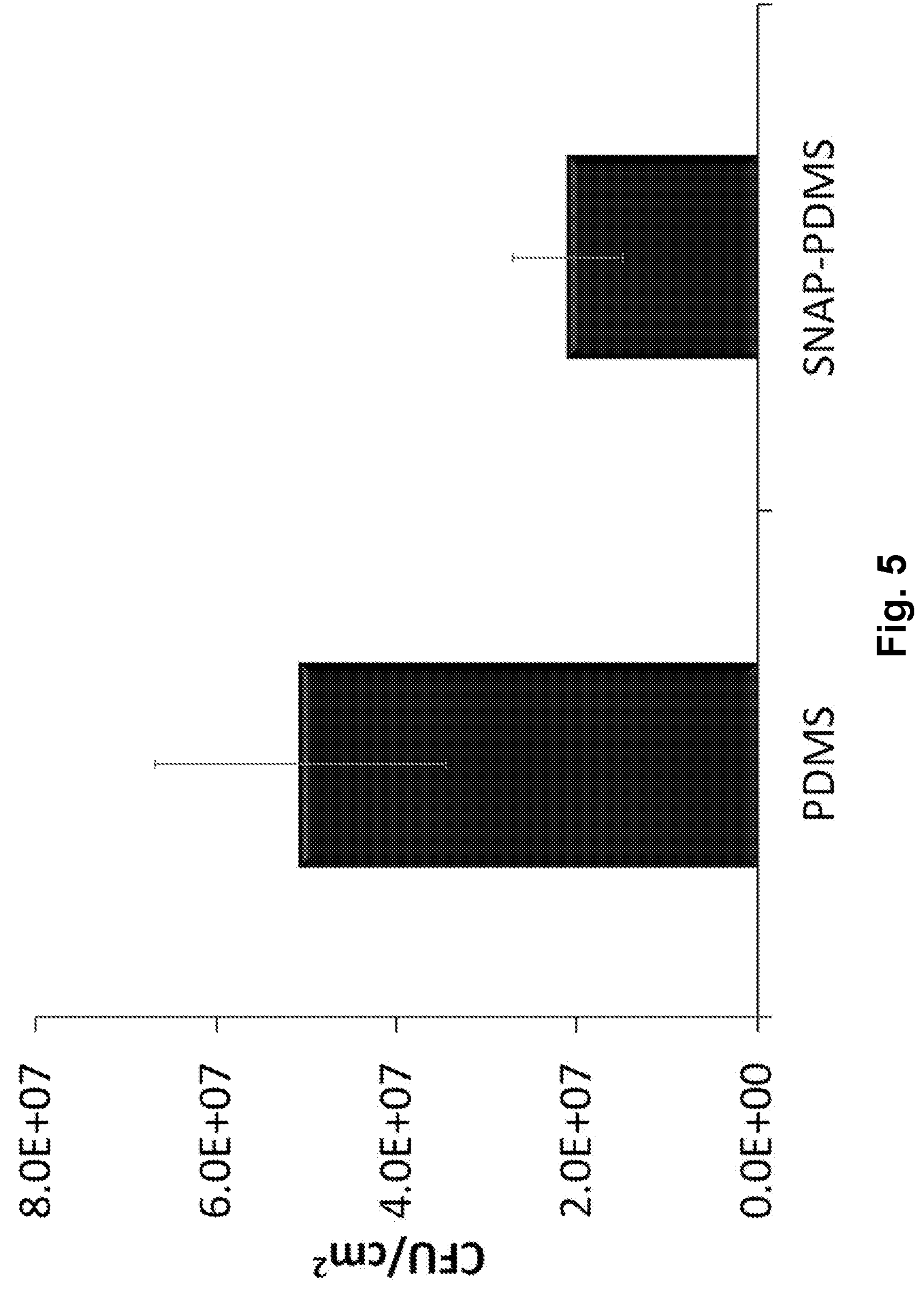
FIG. 5 is a bar graph illustrating examination of the films previously tested for 125 days under physiological conditions (n=3), still demonstrating a 58.6% reduction in viable bacteria. Error bars represent standard deviation.

The SNAP-PDMS films were also tested for their potential antimicrobial abilities after 125 days of sustained release in PBS at 37° C. in a 24 h bacterial adhesion study. Although the end recorded flux of the films were emitting an NO flux of approximately $0.1 \times 10^{-10}$ mol $cm^{-2}$ $min^{-1}$, past studies have demonstrated that these levels of NO can still have antimicrobial effects.[53-54] The SNAP-PDMS films were still able to inhibit the adhesion of *S. aureus* by 58.6% (FIG. 5), giving insight into how even NO fluxes below the normal physiological levels from exogenous NO donating sources can still possess antimicrobial properties.

Cytotoxicity of SNAP-PDMS

Materials that can have any potential leachates could be detrimental to the surrounding cells, so it is important to investigate any possible toxic effects. Using a standard protocol, SNAP-PDMS films were tested for any cytotoxic leachates to cultured mouse fibroblast cells.[44] The SNAP-PDMS films were submerged in DMEM at 37° C. in amber vials for 24 h to allow any leachates from the films to diffuse into the medium. After 24 hrs, the fibroblast cells that were grown in parallel were exposed to the leachates and incubated for the next 24 hrs. The CCK-8 kit based cytotoxicity assay showed that compared with the control PDMS films, more than 96% of fibroblast cells were found to be viable when exposed to the leachates from SNAP-PDMS films. Thus, the cytotoxicity study provides supportive evidence for the potential biocompatibility of SNAP-PDMS films towards mouse fibroblast cells. In the past, different NO releasing materials are shown to be highly effective in inhibiting bacterial growth as well as platelet activation. Having high antibacterial potential is a great advantage for biomedical device fabrication but not at the cost of toxic side-effects on host mammalian cells. Other studies have shown very high doses of antibacterial agents: antibiotics, silver nanoparticles, or NO donors, without validating optimal therapeutic dose which is noncytotoxic to mammalian cells.[23, 55-56] Thus the present study is significant in proving the antibacterial efficacy and antithrombotic potential of NO releasing PDMS films without causing undesired cytotoxic responses. In addition, the morphology of the mouse fibroblast cells was maintained at the end of the study further supporting that there was no alternation in cellular metabolism.

This result was expected as NAP, the precursor of SNAP, is FDA approved and is often used to control heavy metal poisoning.[57-58] Treatments using NAP have also been used to treat cystinuria at levels as high as 2-4 g/day over the course of 155 days.[59] Similar results in the past have been shown where more than 90% of cell viability was exhibited by different NO releasing polymeric composites.[60-62] Further testing in animal models would be helpful to establish in vivo data to reaffirm the efficacy of these materials in pre-clinical settings.

SNAP-PDMS Extracorporeal Circuit Hemocompatibility

Comparison between control PDMS and SNAP-PDMS coated ECC loops were performed in a rabbit model for 4 h (FIGS. 6A-6C). The two major parameters that were investigated for this study were platelet count and thrombus formation. Quantification of these parameters gives insight into how the release of NO from SNAP-PDMS coatings can be used as a method for improving hemocompatibility of blood contacting devices. Platelet count was recorded every hour for the duration of the ECC test and compared to the measured baseline taken before the experiment and corrected for hemodilution. Although SNAP-PDMS has been proven to release for several months, only the first 4 h of hemocompatibility is to be observed with this study to demonstrate its initial effectiveness in an extracorporeal setting.

For silicone rubber coated controls, platelet concentration dropped to ~55% of the baseline levels (n=3), where one control loop clotted prior to the 4 h (FIG. 6A). All NO releasing circuits maintained flow ca. the initial flow through the ECC loop (100 mL $min^{-1}$), with platelet levels at ~75% of the baseline after 4 hr. A previous study where SNAP was swelled into PDMS tubing, platelet count reached as low as 12% of the baseline for control samples over the 4 h period while the NO releasing tubing maintained 62%.[29] The SNAP-PDMS coating demonstrated to perform even better than this strategy of incorporating SNAP due to the high flux of NO that was able to be maintained during the experiment. However, the control PDMS coating used in this study proved to preserve a significant amount of the platelet count compared to pure silicone rubber. It has been shown in the past that both hydroxy-terminated PDMS and the aminosilane crosslinker used have some hemocompatible properties to attribute to this effect.[63-64] Since SNAP is directly added to the aminosilane crosslinker for the NO releasing loops, the aminosilane has very little functionality compared to control loops.

After the study, the amount of thrombus formation inside the loops was analyzed. Thrombus formation was measured by cutting open the thrombogenicity chamber of the ECC and removing any visible clots. Control loops had large amounts of clotting occur during the duration of the study, where the chamber was covered with a thick, dense layer of loosely bound thrombus formation. The SNAP-PDMS coated circuits showed much less clotting with only a thin layer of thrombus that was much more tightly bound to the surface (FIG. 6C). The SNAP-PDMS coated circuits showed a significant reduction (78% less) in overall thrombus mass compared to control PDMS coated circuits (FIG. 6B).

CONCLUSION

In this study, the covalent attachment of SNAP to PDMS was demonstrated to be an effective long term (>4 months) NO releasing material. By eliminating the potential of unwanted leaching of the NO donor into the surrounding environment, the sustained and passive NO release was suitable as both a long duration antimicrobial and short term antithrombotic surface in addition to being non-cytotoxic to mammalian cells. Compared to the traditional method of blending RSNOs into a polymer, the covalent attachment allows no potential leaching of the NO donor into the surrounding environment which is key to its longevity and noncytotoxic effects. The SNAP-PDMS material demonstrated that it was able to significantly inhibit bacterial adhesion of *S. aureus* even after constant exposure for a month in a CDC bioreactor. Even after 125 days of physiological release, the films were able to reduce nearly 60% of the overall bacterial adhesion, showing that the films still retained antimicrobial efficacy with low levels of sustained NO release. The multifunctional ability of NO was further proven as thrombus formation on the inner lumen of ECC loops coated with SNAP-PDMS was also greatly reduced due to the NO releasing SNAP-PDMS, indicating the flexibility of the polymer as a both a hemocompatible surface as well as antimicrobial.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

I claim:

1. A nitric oxide releasing material comprising a polymer matrix, wherein the polymer matrix comprises a plurality of polysiloxanes covalently crosslinked with a plurality of nitric oxide-donating crosslinking moieties;

wherein the nitric oxide-donating crosslinking moieties are present in an amount from about 0.1 micromoles to about 0.801 micromoles per milligram of the polymer matrix;

wherein each of the nitric oxide-donating crosslinking moieties comprise a S-nitroso-N-acetyl-penicillamine group covalently attached thereto; and wherein the plurality of polysiloxanes have a kinematic viscosity of about 2,550 cSt to about 3,570 cSt prior to crosslinked in the polymer matrix.

2. The nitric oxide-releasing material according to claim 1, wherein the polysiloxanes in the plurality of polysiloxanes are selected from the group consisting of polydimethylsiloxane, polydiethylsiloxane, polydipropylsiloxane, and polydiphenylsiloxane.

3. The nitric oxide-releasing material according to claim 1, wherein the nitric oxide-donating crosslinking moieties are present in an amount from about 0.2 micromoles to about 0.801 micromoles per milligram of the polymer matrix.

4. A nitric oxide-releasing material produced the method comprising:

crosslinking a plurality of polysiloxanes with a plurality of amine-functionalized crosslinking moieties to produce a crosslinked polymer matrix;

covalently attaching a thiolactone to an amine in the amine-functionalized crosslinking moieties to produce a thiol-functionalized crosslinked polymer matrix; and nitrosating the thiol in the thiol-functionalized crosslinked polymer matrix in the presence of an organic acid to produce the nitric oxide-releasing material comprising nitric oxide-donating crosslinking moieties, wherein the nitric oxide-donating crosslinking moieties are present in an amount from about 0.1 micromoles to about 0.801 micromoles per milligram of the polymer matrix;

wherein each of the nitric oxide-donating crosslinking moieties comprise a S-nitroso-N-acetyl-penicillamine group covalently attached thereto; and wherein the plurality of polysiloxanes have a kinematic viscosity of about 2,550 cSt to about 3,570 cSt prior to crosslinked in the polymer matrix.

5. A method for making a nitric oxide-releasing material the method comprising:

crosslinking a plurality of polysiloxanes with a plurality of amine-functionalized crosslinking moieties to produce a crosslinked polymer matrix;

covalently attaching a thiolactone to an amine in the amine-functionalized crosslinking moieties to produce a thiol-functionalized crosslinked polymer matrix; and nitrosating the thiol in the thiol-functionalized crosslinked polymer matrix in the presence of an organic acid to produce the nitric oxide-releasing material comprising nitric oxide-donating crosslinking moieties, wherein the nitric oxide-donating crosslinking moieties are present in an amount from about 0.1 micromoles to about 0.801 micromoles per milligram of the polymer matrix;

wherein each of the nitric oxide-donating crosslinking moieties comprise a S-nitroso-N-acetyl-penicillamine group covalently attached thereto; and wherein the plurality of polysiloxanes have a kinematic viscosity of about 2,550 cSt to about 3,570 cSt prior to crosslinked in the polymer matrix.

6. The nitric oxide-releasing material according to claim 4, wherein the organic acid comprises dodecylbenzene sulfonic acid, dinonylnaphthalenedisulfonic acid, 4-octylbenzenesulfonic acid, acetic acid, formic acid, or lactic acid.

7. The nitric oxide-releasing material according to claim 4, wherein the organic acid is dodecylbenzene sulfonic acid.

8. The nitric oxide-releasing material according to claim 4, wherein the amine-functionalized crosslinking moieties have a structure according to the following formula

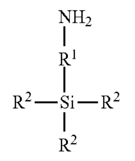

where $R^1$ is selected from a substituted or unsubstituted $C_1$-$C_{20}$ alkyl, a substituted or unsubstituted $C_1$-$C_{20}$ heteroalkyl, a substituted or unsubstituted $C_2$-$C_{20}$ alkenyl, a substituted or unsubstituted $C_2$-$C_{20}$ heteroalkenyl, a substituted or unsubstituted $C_1$-$C_{20}$ alkoxy, or a substituted or unsubstituted $C_1$-$C_{20}$ heteroalkoxy;

where each occurrence of $R^2$ is hydroxy or alkoxy.

9. The nitric oxide-releasing material according to claim 8, wherein each occurrence of $R^2$ is a hydroxy, methoxy or ethoxy.

10. The nitric oxide-releasing material according to claim 8, wherein $R^1$ is a substituted or unsubstituted $C_1$-$C_{12}$ alkyl or a substituted or unsubstituted $C_1$-$C_{12}$ aminoalkyl.

11. The nitric oxide-releasing material according to claim 10, wherein the thiolactone has a structure according to the following formula

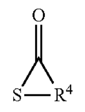

where $R^4$ is a substituted or unsubstituted $C_1$-$C_{12}$ alkyl.

12. The nitric oxide-releasing material according to claim 4, wherein the thiolactone has a structure according to the following formula

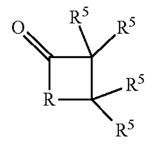

where each occurrence of $R^5$ is independently a hydrogen, a hydroxyl, a substituted or unsubstituted $C_1$-$C_6$ alkyl, substituted or unsubstituted $C_1$-$C_6$ heteroalkyl, a substituted or unsubstituted $C_2$-$C_6$ alkenyl, a substituted or unsubstituted $C_2$-$C_6$ heteroalkenyl, a substituted or unsubstituted $C_1$-$C_6$ alkoxy, or a substituted or unsubstituted $C_1$-$C_6$ heteroalkoxy.

13. The nitric oxide-releasing material according to claim 4, wherein the thiolactone is N-acetyl-D-penicillamine or a derivative thereof.

14. The nitric oxide-releasing material according to claim 4, wherein the thiolactone is selected from the group consisting of N-acetylcysteine thiolactone, N-acetyl-homocysteine thiolactone, homocysteine thiolactone, and butyrylhomocysteine thiolactone.

15. A device having at least one surface, wherein the at least one surface comprises a nitric oxide-releasing material according to claim 1.

16. The device according to claim 15, wherein the device comprises a rubber material having the nitric oxide-releasing material dispersed within the rubber.

17. The device according to claim 16, wherein the rubber is a silicone rubber.

18. The device according to claim 15, wherein the nitric oxide-releasing material is applied to a surface of a substrate.

19. The device according to claim 18, wherein the substrate is selected from a polymer, a metal or a glass.

20. The device according to claim 15, wherein the device is a urinary catheter, artificial heart valve, a vascular catheter, a graft, or a stent.

21. The device according to claim 15, wherein the device is intended to contact human blood or tissue.

22. The device according to claim 21, wherein the device is a hemodialysis device or a component thereof.

23. The device according to claim 15, wherein the device is an implantable medical device.

24. The device according to claim 15, wherein the device is an anti-biofilm invoking surface.

25. A method of reducing blood clotting or adhesion of a biomaterial to a surface, the method comprising applying the nitric oxide-releasing material according to claim 1 to the surface.

26. A method of reducing biofilm formation on a surface of an article, the method comprising applying the nitric oxide-releasing material according to claim 1 to the surface.

* * * * *